United States Patent [19]

Bush et al.

[11] 4,419,879
[45] Dec. 13, 1983

[54] PARTICLE MEASURING APPARATUS

[75] Inventors: Darrell C. Bush, Colleyville; Ralph E. Jenkins, Irving, both of Tex.

[73] Assignee: Core Laboratories, Inc., Dallas, Tex.

[21] Appl. No.: 312,107

[22] Filed: Oct. 16, 1981

[51] Int. Cl.³ .................... G01N 15/02; G01N 15/04
[52] U.S. Cl. .............................. 73/432 PS; 177/245; 364/555
[58] Field of Search .................... 73/432 PS, 61.4; 364/555; 177/245

[56] References Cited

U.S. PATENT DOCUMENTS

| Re. 28,940 | 8/1976 | Komline, Sr. et al. | 73/61.4 |
|---|---|---|---|
| 2,845,793 | 8/1958 | Cardwell | 73/53 |
| 3,208,286 | 9/1965 | Richard | 73/432 PS |
| 3,269,189 | 8/1966 | Monk | 73/432 PS |
| 3,519,353 | 7/1970 | Franz et al. | 356/102 |
| 3,583,209 | 6/1971 | Banks | 73/32 |
| 3,756,400 | 9/1973 | Kammori et al. | 73/432 PS |
| 3,812,966 | 5/1974 | Beach et al. | 73/61.4 X |
| 3,830,969 | 8/1974 | Hofstein | 356/197 |
| 3,869,903 | 3/1975 | Beach et al. | 73/614 |
| 3,896,660 | 7/1975 | Valentyik | 73/61.4 |
| 3,914,058 | 10/1975 | Knapp et al. | 356/197 |
| 4,079,621 | 3/1978 | Batzar | 73/432 PS X |
| 4,178,796 | 12/1979 | Zwicker et al. | 73/61.4 X |
| 4,205,384 | 5/1980 | Merz et al. | 364/555 |
| 4,282,745 | 8/1981 | Burr | 73/432 PS |
| 4,353,795 | 10/1982 | Romanauskas | 73/432 PS X |

FOREIGN PATENT DOCUMENTS 2251838  7/1975  Fed. Rep. of Germany ... 73/432 PS

OTHER PUBLICATIONS

Publ., "Particle Size Determination" by R. D. Cadie: pp. 194–207, TA 406.7 (1955).

Primary Examiner—Daniel M. Yasich
Attorney, Agent, or Firm—Lee C. Robinson, Jr.

[57] ABSTRACT

A particle size analyzer of the sedimentation type in which a cup-shaped member is used to deposit the particles in the sedimentation fluid substantially simultaneously and at low velocity. The particles are ultrasonically dispersed as they are deposited in the fluid and are collected by a balance member which detects their receipt as a function of time. An electronic circuit connected to the balance member determines the size of the particles through the use of Stokes' Law and an empirically determined relationship between the settling velocity of the particles and their size.

19 Claims, 7 Drawing Figures

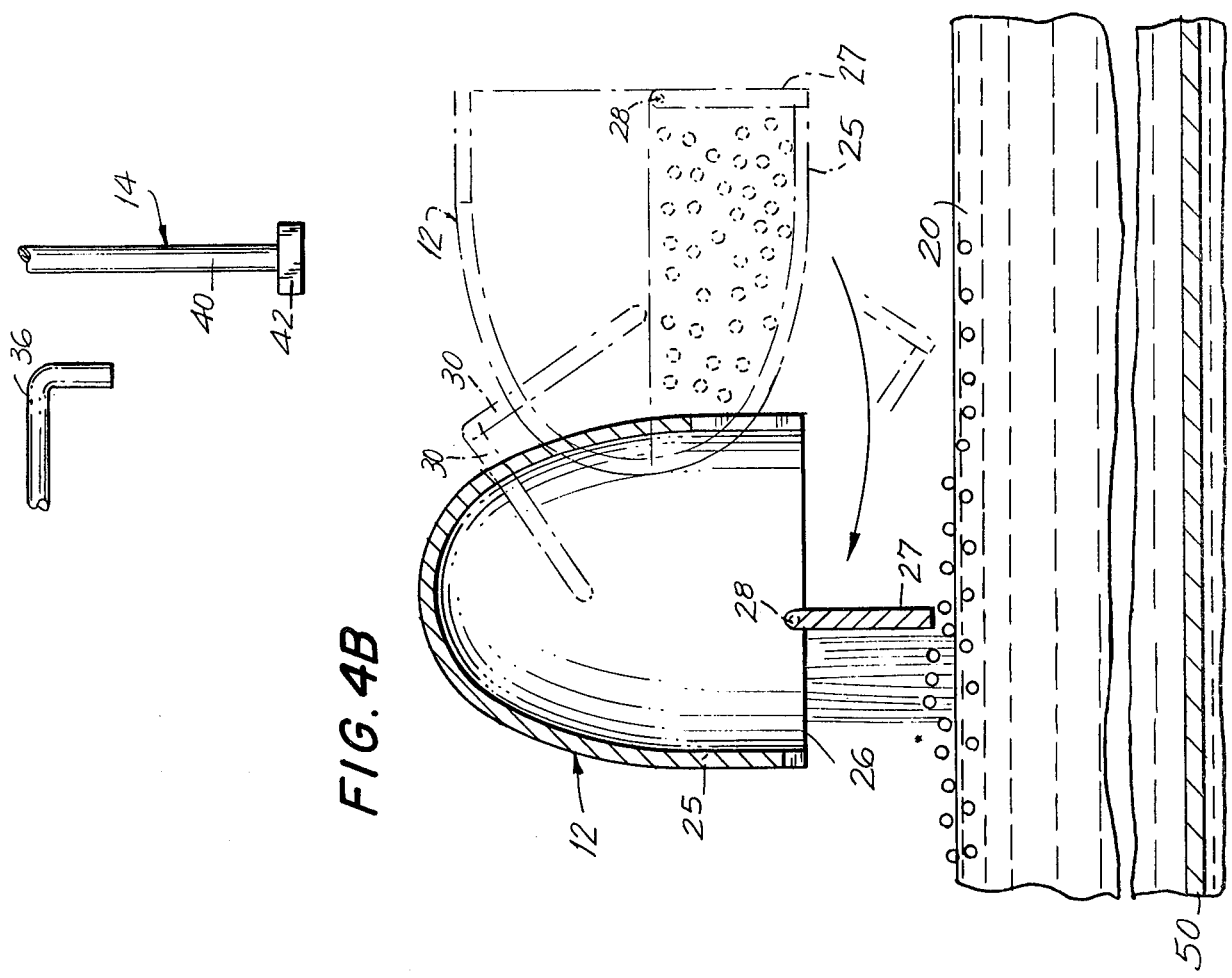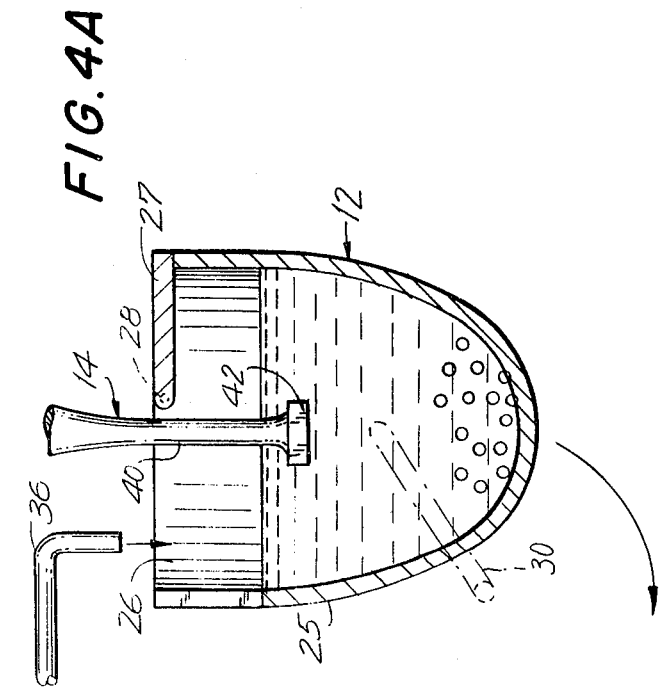

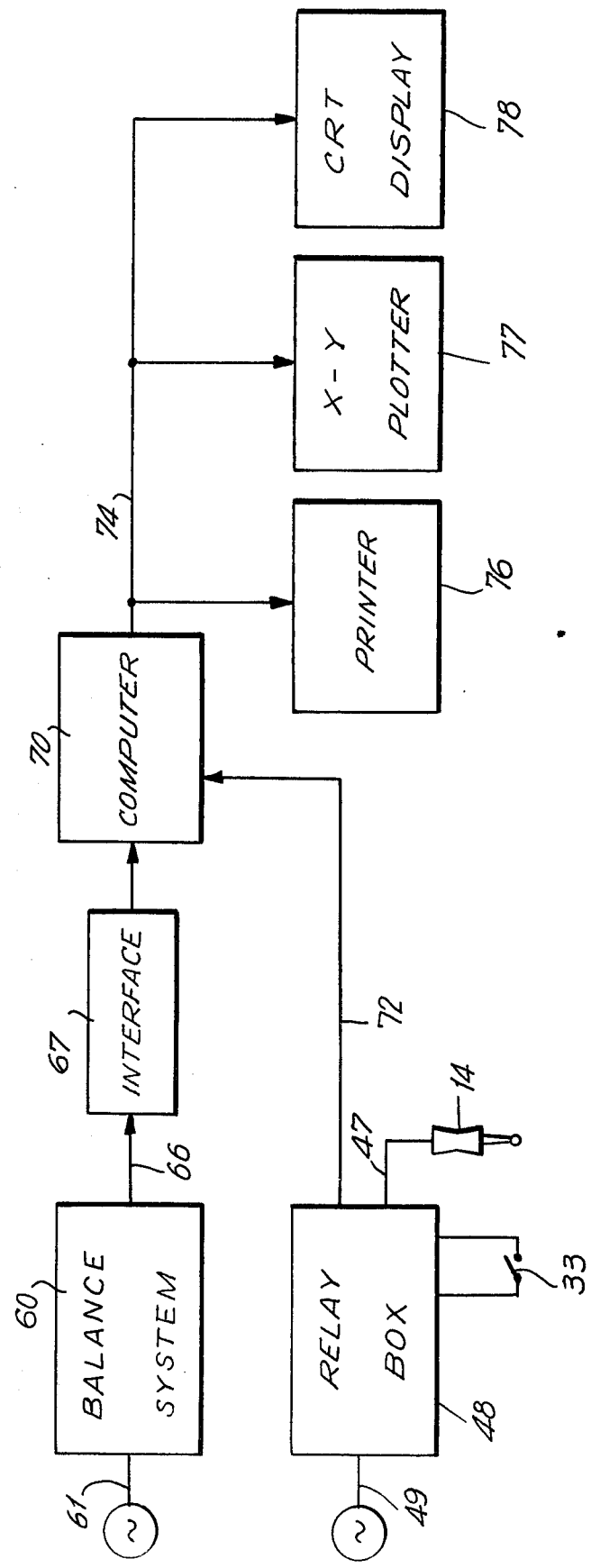

PARTICLE MEASURING APPARATUS

BACKGROUND OF THE INVENTION

This invention relates to measuring apparatus and more particularly to apparatus for measuring the size of solid particles falling in a fluid of known viscosity.

There are a number of presently available techniques for ascertaining the dimensions of small particles. These have included, in addition to the well known sieve or screen analyses, the measurement of the particles microscopically, sedimentation techniques, permeability systems, adsorption and photo-extinction. In the oil and gas field, for example, the measurement of rock and sand particles, etc., commonly is accomplished by passing the particles through a series of screens of different sizes to obtain a rough quantification of the size of the particles retained on each screen. For particles in the less than fine sand size range or in other cases in which more rapid particle size information is desired, however, the screen analysis technique has proven deficient, and it frequently is desirable to turn to one or more of the other available measuring systems. Also, most sedimentary rocks were deposited by water, and it is highly desirable to use a closely related technique in the particle size analysis of such rocks.

Sedimentation techniques are generally more reliable and accurate than some of the other methods for determining the size of the smaller size particles. The sedimentation techniques are based in whole or in part on the well known Stokes' Law relating the velocity of the particles settling in a fluid to the size and density of the particles and the viscosity and density of the fluid. By making certain simplifying assumptions the particle size may be ascertained in a reasonably straightforward manner without the need for tedious microscopic examination of the particles or overly expensive and sophisticated equipment.

The sedimentation techniques and equipment employed heretofore, however, have exhibited a number of disadvantages. As an illustration, when using several types of prior techniques and apparatus for this purpose the particles often agglomerated or were otherwise unevenly dispersed at the time of deposition with the result that the overall accuracy of the measurements was impaired. Furthermore, and this has been of special moment in analyzing core samples and in other instances where there is a need for prompt and accurate particle size data, the amount of time required for making the measurements was excessive in many instances.

SUMMARY

One general object of this invention, therefore, is to provide new and more efficient sedimentation apparatus and techniques for measuring the size of solid particles falling in a fluid of known viscosity.

More specifically, it is an object of this invention to provide such apparatus and techniques in which the resulting measurements are suitably reliable for many petrophysics applications.

Another object of the invention is to provide measuring apparatus and techniques of the character indicated in which the size of the particles being measured may be determined more rapidly than with sedimentation systems of the type used heretofore.

A further object of this invention is to provide apparatus for measuring the size of solid particles in which the apparatus has comparatively simple mechanical and electrical components and is economical to manufacture and straightforward in operation.

In one illustrative embodiment of the invention, the apparatus includes a sedimentation container for a column of distilled water or other fluid of known viscosity. A particle dispenser is disposed above the fluid in the container, and a balance member is suspended in the container. The particle dispenser is supported for unique swinging movement immediately above the surface of the fluid column to discharge the particles into the fluid where they settle and are received by the balance member. An electrical circuit connected to the balance member times the fall of the particles and determines their size from the calculated settling velocities.

In accordance with one feature of the invention, in certain particularly important embodiments, the particle dispenser is of cup-shaped or hemi-ellipsoidal configuration. The dispenser is supported for swinging movement immediately above the surface of the fluid in the sedimentation container and is effective to rapidly and substantially simultaneously transfer all of the particles thereto. The arrangement is such that the particles enter the fluid at a slow velocity. The electrical circuit is effective to determine the settling velocities on the basis of the time and distance travelled before constant particle velocities have been achieved. With this arrangement, the size of the particles may be determined with suitable accuracy and more rapidly than with sedimentation systems of the type previously employed.

In accordance with another feature of the invention, in several important arrangements, the particles are dispersed through ultrasonic techniques. The dispersal of the particles is effective to ensure a more even particle distribution at the time or shortly after the particles come in contact with the surface of the fluid and provides a substantial improvement in the overall accuracy of the resulting measurements. Also, the ultrasonic energy tends to dislodge clay coatings that frequently are tightly attached to the particles, allowing a more accurate particle size analysis of the sample.

In accordance with a further feature of some embodiments of the invention, the particle dispenser is provided with an open mouth portion and a lid pivotally carried by the dispenser and extending over only a part of the open mouth portion. During a rapid but smooth swinging movement of the dispenser the lid inhibits the premature discharge of the particles until after the dispenser has moved through an angle of about ninety degrees. The lid then pivots to its open position to spread all of the particles on the liquid surface at substantially the same time. As a result, the overall accuracy of the apparatus is further enhanced.

The foregoing and other objects, features and advantages of the invention will be more readily understood from the following description of certain preferred embodiments, when read with reference to the accompanying drawings.

BRIEF DESCRIPTION OF THE DRAWINGS

FIG. 4A is an enlarged fragmentary sectional view of the particle dispenser of the apparatus, together with certain associated components.

FIG. 4B is an enlarged fragmentary sectional view similar to FIG. 4A but showing the particle dispenser as it swings to discharge the particles into the container.

FIG. 6 is a schematic block diagram of an electrical circuit useful in connection with the apparatus.

DESCRIPTION OF CERTAIN PREFERRED EMBODIMENTS

The determination of particle size by means of sedimentation techniques is based on the well known principle that small particles suspended in a fluid medium settle with a constant velocity when the fluid resistance force is equal to the downward constant force of gravity acting on the particles. The settling velocities of the particles depend on the surface texture, radius, shape and density of the particles and on the density and viscosity of the fluid.

Stoke's Law is a mathematical expression relating these factors:

$$R = 6\pi rnv = (4/3)\pi r^3(d_1 - d_2)g$$

$R$ = resistance in g.cm/sec$^2$ of fluid to movement of suspended spherical particles
$r$ = radius of sphere in cm
$n$ = viscosity of the fluid in poises
$v$ = velocity of the sphere in cm/sec
$d_1$ = density of spherical particles, g./cm$^3$
$d_2$ = density of fluid, g./cm$^3$
$g$ = acceleration of gravity, cm/sec$^2$.

By utilizing a suspending fluid of a known viscosity and by knowing the density of the fluid and of the particles being measured, the velocity of the particles may be detected to determine the radius or particle size.

Rather than attempting to achieve a constant velocity for the particles, the apparatus described herein initiates the introduction of the particles into the fluid at a slow velocity and then detects the mean or average velocity as the particles drop through the fluid over a known but comparatively short distance.

In addition, although the measurement of the particles by Stokes' Law assumes that the particles are spherical and have smooth friction-free surfaces, the described apparatus advantageously uses an empirical data bank of settling velocity versus median particle size for particles with shapes more similar to the particles to be evaluated.

Figure 1:
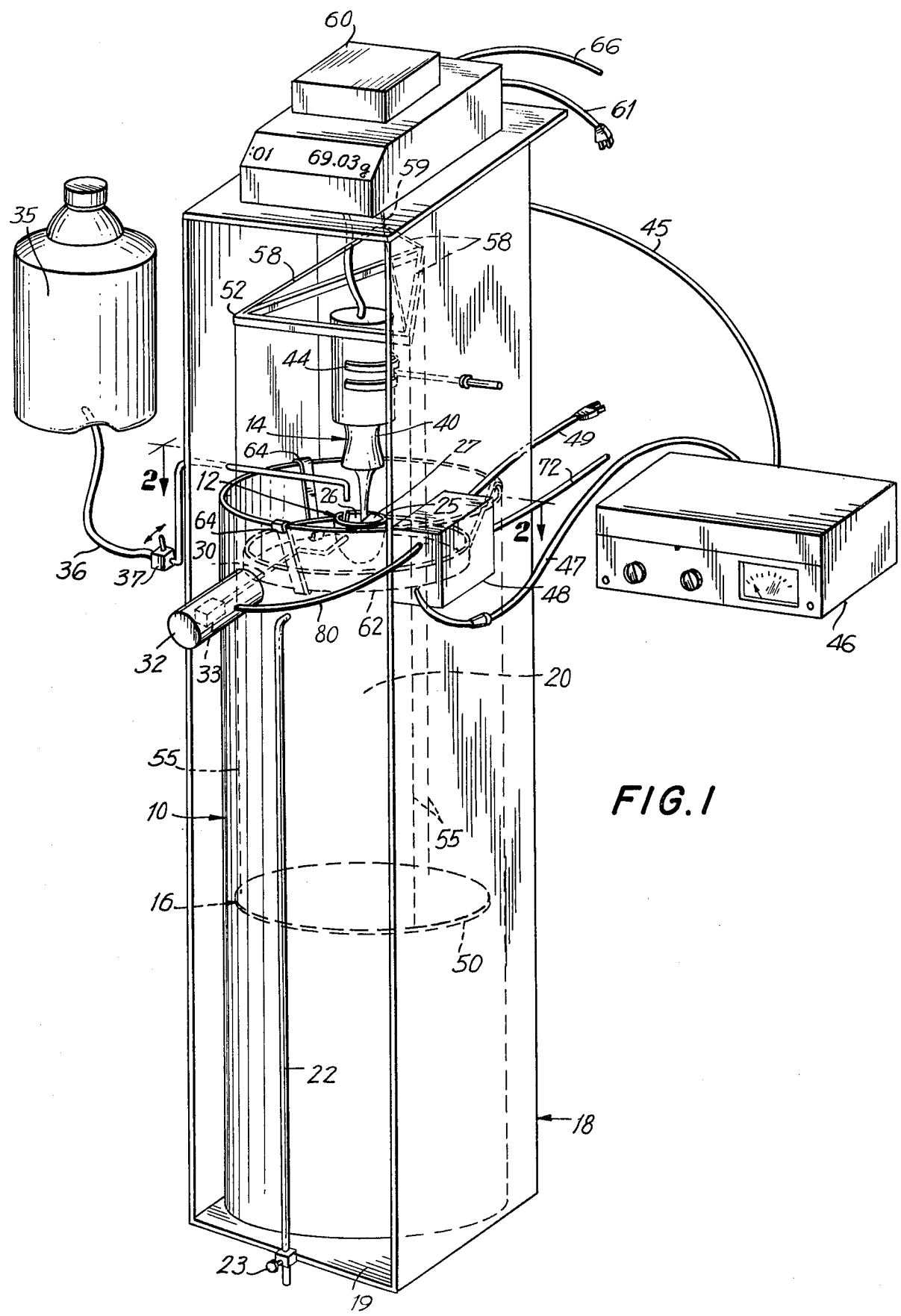
FIG. 1 is a perspective view of apparatus for measuring the size of solid particles in accordance with one illustrative embodiment of the invention.
Figure 2:
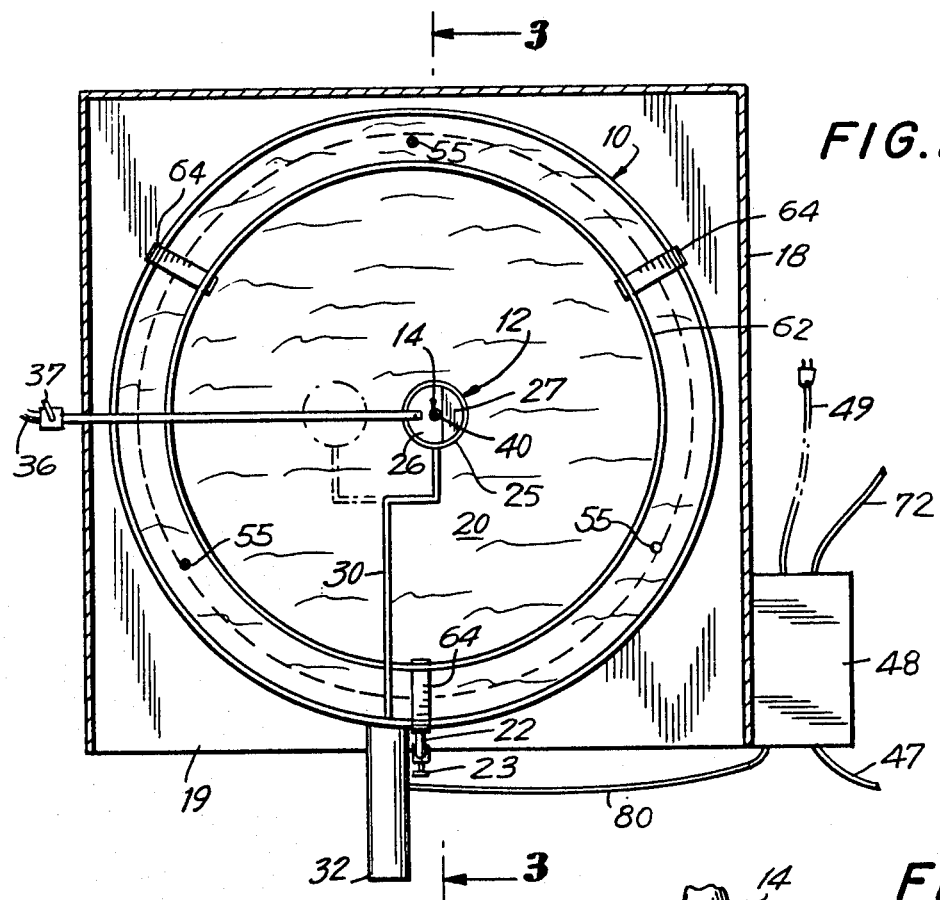
FIG. 2 is a transverse sectional view of the apparatus taken along the line 2—2 in FIG. 1.

Referring now to FIG. 1 of the drawings, there is shown an apparatus for accomplishing this result. The apparatus includes a sedimentation container 10 for the known viscosity fluid, a particle dispenser 12 disposed above the fluid in the container, an ultrasonic transducer 14 for dispersing the particles and a balance system 16 suspended in the container for receiving the dispensed particles. These components are mounted within an upstanding cabinet 18 which is closed on three sides but has an open front 19 to permit ready access to the apparatus. The cabinet 18 illustratively is of aluminum and may be provided with a door (not shown) adjacent the upper portion of the open front 19 to prevent ambient air currents from disturbing the particles and the fluid.

The sedimentation container 10 is in the form of an upstanding cylinder or tube containing a column of fluid 20 of known viscosity. The container 10 illustratively is of transparent plastic material with an outside diameter of ten inches, a length of thirty inches and a wall thickness of one-fourth inch. Although a wide variety of known viscosity fluids may be used in the container 10, distilled water is preferred because of its easily determinable properties and ready availability. A constant length water column is maintained by an overflow conduit 22 which communicates with the upper portion of the container and which extends downwardly into a drain (not shown) a short distance beneath a suitable stopcock valve 23.

Positioned immediately above the surface of the fluid 20 in the sedimentation container 10 is the particle dispenser 12. The dispenser 12 includes a cup-shaped or hemi-ellipsoidal sample container 25 having an open mouth 26 and a lid 27. As best shown in FIG. 4A, in the upright position of the container 25 the lid 27 extends over only a part of the open mouth 26 and is pivotally secured to the inner upper periphery of the container by a shaft 28. When the lid is in its closed, FIG. 4A, position, it covers approximately one-half of the container mouth.

The sample container 25 is supported at the inner end of a crank arm 30. The arm 30 extends through a suitable aperture in the cylindrical wall of the sedimentation container 10 and is provided at its outer end with a hollow handle 32 containing a mercury switch 33. By manually rotating the handle 32 the sample container 25 may be swung to an inverted position as a result of the crank arm 30. As the container passes through an angle of approximately ninety degrees, the switch 33 closes for purposes that will become more fully apparent hereinafter.

A tank 35 is suitably supported adjacent the cabinet 18 above the level of the sample container 25. The tank 35 contains distilled water and a wetting agent and is provided with a discharge conduit 36 leading to a position a short distance above the sample container 25. The flow of wetting agent and water from the tank to the sample container is controlled by a stopcock valve 37 in the conduit 36.

The ultrasonic transducer 14 comprises a horn 40 which is suspended above the particle dispenser 12 such that the horn's tip 42 (FIG. 4A) protrudes into the open mouth 26. The horn 40 is mounted on a support clamp 44 affixed to the upper side wall of the cabinet 18 and is electrically connected by a cable 45 to an ultrasonic generator 46. As will be understood, the generator 46 is effective to energize the horn 40 to vibrate the tip 42 (FIG. 4a) at an ultrasonic frequency, illustratively 20,000 Hz. The horn 40 and the generator 46 may be of conventional construction and in the illustrated embodiment comprise the Model 185 Sonifier available commercially from the Branson Sonic Power Co., Danbury, Conn. The generator 46 is supplied with power from a power cord 47 leading to a relay box 48 mounted on the side wall of the cabinet 18. Power from a suitable alternating current source (not shown in FIG. 1) is supplied to the relay box 48 by a power cord 49.

A sample collecting pan 50 is suspended within the sedimentation container 10 and forms a part of the balance system 16. The pan 50 is of circular configuration and illustratively may be fabricated from acrylic plastic. The pan 50 is located a known distance beneath the upper surface of the column of fluid 20 and is supported by three filament wires 55 connected to the corners of a spacer triangle 52. The triangle 52 is suspended a short distance above the ultrasonic transducer 14 by three chains 58 connected to the hook 59 of a balance unit 60 forms the weight-computing part of the balance system 16, and mounted on the top of the cabinet 18. The unit 60 may be of conventional construction and illustratively is of the type available commercially from the Mettler Instrument Corp., Heightstown, N.J., and identified as its Model PK300. The unit 60 is supplied with electrical power from a line cord 61 and produces varying output signals proportional to the weight of the particles on the pan 50 of the system 16.

Figure 3:
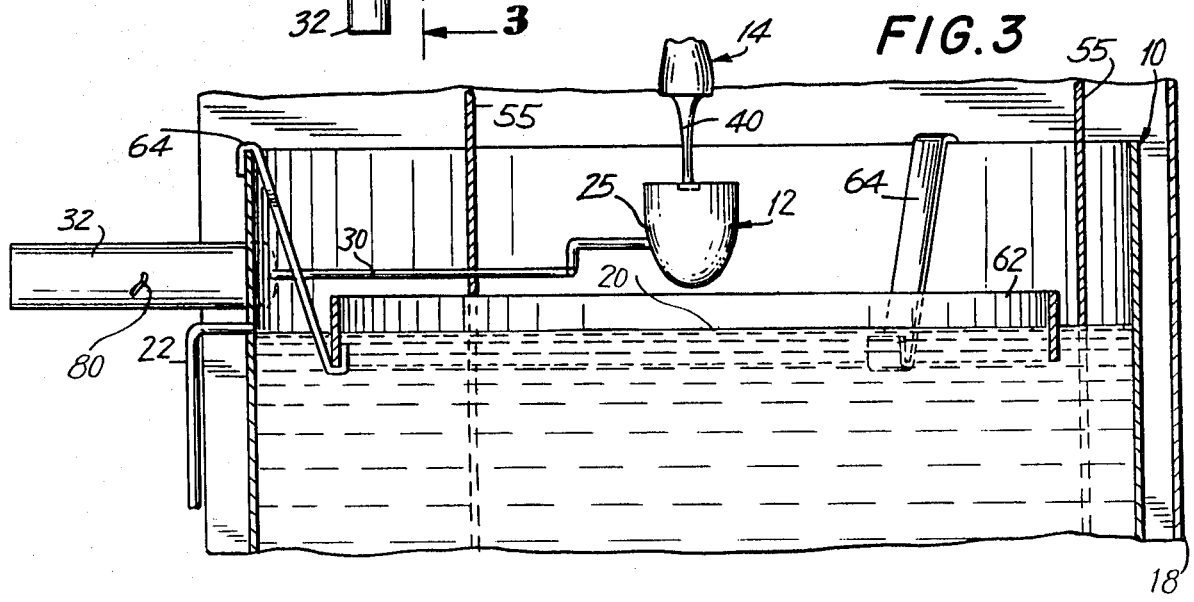
FIG. 3 is a fragmentary sectional view taken along the line 3—3 of FIG. 2.

A ring-shaped wave-suppressing member 62 is supported within the container 10 at the level of the upper surface of the water column 20. The member 62 is affixed to the upper peripheral edge of the container 10 by three straps 64. Approximately one-half of the vertical height of the member 62 is submerged in the column 20 such that the upper surface of the column outside of the suspended ring remains smooth and ripple free. As best shown in FIG. 3, the pan supporting filaments 55 are externally disposed with respect to the member 62. The arrangement is such that the member 62 isolates the filaments 55 and prevents their disturbance when the sample being tested is introduced into the column.

The various electrical components of the apparatus are connected in a circuit schematically illustrated in FIG. 6. Data representing the particle weight sensed by the balance unit 60 are transmitted over a line 66 and an interface circuit 67 to a computer 70. The computer 70 operates under the control of the relay box 48 and is connected thereto by a line 72. The computer is of conventional construction and is provided with a suitable timing circuit to detect the incoming weight information from the balance unit 60 at uniform timed intervals up to the total time selected by the operator of the apparatus. The computer is programmed to determine the particle size data according to Stokes' Law using the empirical settling velocities discussed heretofore, and these data appear of an output lead 74. The lead 74 is connected to a printer 76 to record the output data, an X-Y plotter 77 to provide a graphic display of the data and a cathode ray tube display 78 which serves as a visual display.

The sample of paticles to be evaluated is prepared for testing by cleaning the particles of hydrocarbons, salt, etc., and then obtaining their air suspended dry weight. The dry weight is entered in the computer 70 together with the smallest particle size for which a measurement is desired and the length of the column of fluid within the container 10, that is, the vertical distance from the fluid surface to the sample collecting pan 50. The computer also contains information as to settling velocities versus grain size for the type of particles being measured (e.g. nonspherical particles), the viscosity of the sedimentation fluid, the date and time of the test and other desired identifying data.

The thus prepared particles are inserted into the sample container 25. The stopcock valve 37 is opened to introduce a suitable wetting solution in distilled water from the tank 35 through the conduit 36 into the container 25. As best shown in FIG. 4A, the quantity of particles and solution introduced into the container 25 is such that the surface level of particles and solution is located a short distance above the tip 42 of the ultrasonic horn 40.

The ultrasonic generator 46 is then energized to vibrate the horn 40 and thereby wet the sample particles and also evenly disperse the particles within the dispensing container 25. Within a short period of time, illustratively fifteen seconds, after the energization of the generator 46, the handle 32 is rapidly rotated in a clockwise direction, as viewed in FIGS. 4A and 4B, through an angle of one hundred and eighty degrees to swing the container 25 through a similar angle from the position shown in FIG. 4A to that illustrated in FIG. 4B. During the initial portion of this swinging movement, the lid 27 remains in its closed position to maintain the particles within the container 25. As the container passes through an angle of approximately ninety degrees and approaches its inverted position, the force of gravity and the liquid in the container causes the lid 27 to swing open and substantially simultaneously deposit all of the particles within the container onto the surface of the fluid 20. The container 25 is located in close proximity with the fluid surface, and because of this rapid movement and the even dispersal of the particles by the ultrasonic horn 40 the particles come in contact with the surface at a uniform and slow vertical velocity.

As the handle 32 is rotated to move the dispensing container 25 through an angle of ninety degrees, the mercury switch 33 closes to energize selected relays in the box 48. These relays simultaneously and automatically turn off the ultrasonic transducer 14 and activate the computer 70 (FIG. 6) to zero the balance system 16 and to initiate the computer program.

Upon the closing of the mercury switch 33 the computer 70 automatically begins recording weights from the balance system 16 at preselected uniform timed intervals, illustratively five seconds, for a period of time sufficient to enable all of the particles from the dispenser 12 to move by gravity through the fluid column 20 and reach the particle receiving pan 50. For the common sands and shales the grain density stored in the computer is 2.65 gm/cm$^3$, and for distilled water in the column the stored fluid density is 1.0 gm/cm$^3$. The computer calculates the percent of each grain size received by the pan 50 according to Stokes' Law using the stored settling velocity versus grain size information and the calculated data appears on the output line 74 and is recorded by the printer 76 and the plotter 77. In addition, the CRT display 78 provides a visual indication of the particle size distribution.

Figure 5:
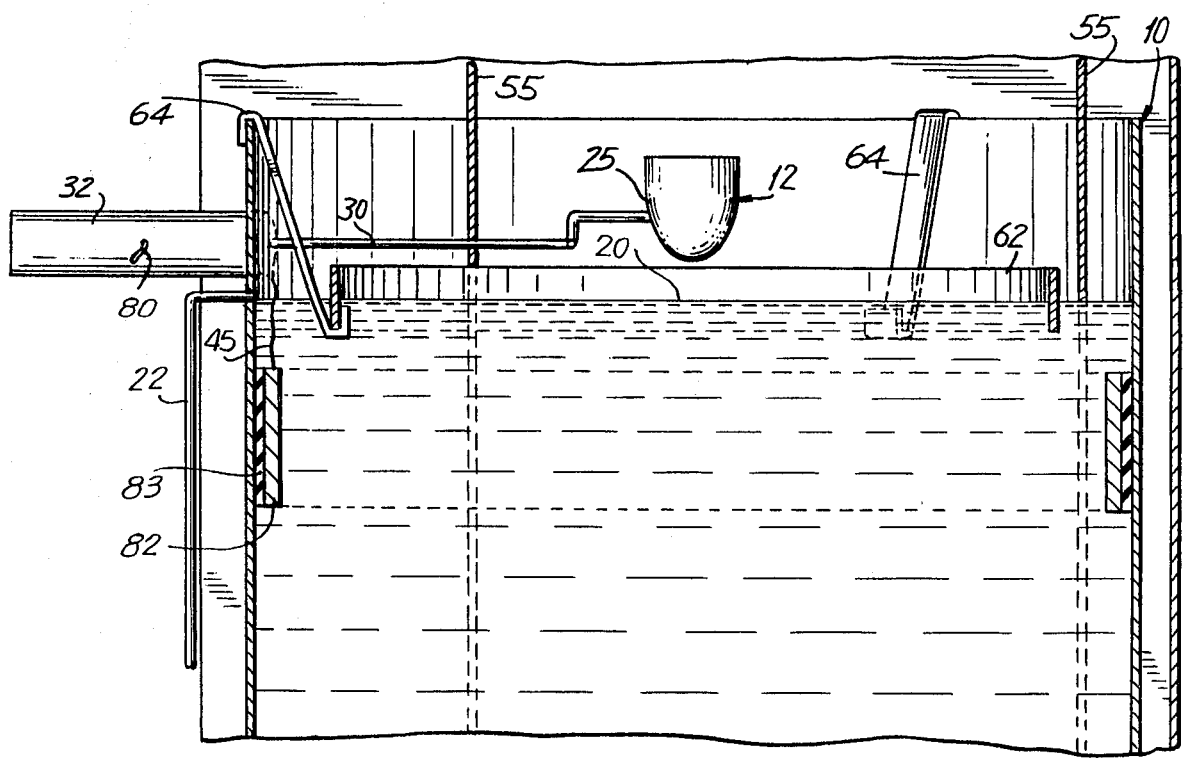
FIG. 5 is an enlarged fragmentary sectional view of a particle dispenser in accordance with another illustrative embodiment of the invention.

FIG. 5 is illustrative of an alternative vibratory ultrasonic transducer 82 useful in connection with the invention. The transducer 82 is in the shape of an open cylinder or ring and is affixed to the inner periphery of the sedimentation container 10 immediately beneath the level of the fluid 20. A suitable layer 83 of insulating material separates the transducer 82 from the wall of the container. The transducer is supplied with power over the cable connected to the ultrasonic generator 46 (FIG. 1) to vibrate the transducer at an ultrasonic frequency and thereby evenly disperse the solid particles as they descend in the fluid through the transducer. The frequency and amplitude of the vibrations are selected so as to disperse the particles without influencing the balance pan 16.

Among its other advantages, the apparatus described and illustrated herein is effective to determine the size of the solid particles in an extremely rapid manner. As an illustration, for particles having a size of up to 0.063 mm the measurements can be completed in less than one minute in a water column of 30.8 cm., while the time required to perform equivalent measurements on smaller particles down to 0.044 mm is approximately 1.35 minutes. The resulting measurements also exhibit good accuracy and repeatability.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. Sedimentation-type particle size measuring apparatus for measuring the size of solid particles falling in a fluid of known viscosity, the apparatus comprising, in combination:
    a sedimentation container for the known-viscosity fluid;
    a cup-shaped particle dispenser initially containing a sample of solid particles and disposed above the fluid in the sedimentation container;
    swingable support means supporting the particle dispenser for swinging movement and selectively actuable for swinging said particle dispenser so that the latter discharges said solid particles immediately above the surface of the fluid in the sedimentation container, thereby rapidly transferring said solid particles from said dispenser to said sedimentation container;
    means including a particle receiving member supported in the fluid in the sedimentation container for detecting the landing thereon of solid particles transferred from said dispenser; and
    means responsive to the detection of the landing of said solid particles onto the particle receiving member for determining the size of the received particles.

2. Apparatus as defined in claim 1, in which the swinging movement of the particle dispenser transfers the particles therein substantially simultaneously to the surface of said fluid such that the particles reach said surface at a slow velocity.

3. Apparatus as defined in claim 1, in which said cup shaped particle dispenser is swung along a substantially horizontal axis by said swingable support means such that said sample of said solid particles is distributed onto the surface of said liquid as an opening in said particle dispenser sweeps across the surface thereof.

4. Apparatus as defined in claim 1, in which the means responsive to the detection of the landing of said solid particles is operative to signal any weight differences of said particle receiving member at timed intervals beginning with the actuation of said swingable support means to dispense the sample of particles.

5. Sedimentation-type particle size measuring apparatus for measuring the size of solid particles falling in a fluid of known viscosity, the apparatus comprising, in combination:
    a sedimentation container for the known-viscosity fluid;
    a particle dispenser for initially containing a sample of solid particles and disposed above the fluid in the sedimentation container;
    swingable support means supporting the particle dispenser for swinging movement and selectively actuable for swinging said particle dispenser so that the latter discharges said solid particles immediately above the surface of the fluid in the sedimentation container, and thereby rapidly transfers said solid particles from said dispenser to said sedimentation container;
    ultrasonic means for dispersing said solid particles;
    balance means including a particle receiving member suspended in the fluid in the sedimentation container for detecting the landing thereon of solid particles transferred from said dispenser; and
    means including an electrical circuit connected to the balance means for timing the landing of solid particles thereon and for determining the size of such particles.

6. Apparatus as defined in claim 5, in which the particle dispenser is of hemi-ellipsoidal configuration.

7. Apparatus as defined in claim 5, in which the operating means inverts the particle dispenser to transfer the solid particles to the sedimentation container.

8. Sedimentation-type particle size measuring apparatus for measuring the size of solid particles falling in a fluid of known viscosity, the apparatus comprising, in combination:
    a sedimentation container for the known-viscosity fluid;
    a cup-shaped particle dispenser for initially containing a sample of solid particles and disposed above the fluid in the sedimentation container;
    ultrasonic means cooperating with the particle dispenser for dispersing solid particles therein;
    swingable support means supporting the particle dispenser for swinging movement and selectively actuable for swinging said particle dispenser so that the latter discharges said solid particles immediately above the surface of the fluid in the sedimentation container, and thereby rapidly transfers said solid particles from said dispenser to said sedimentation container;
    balance means including a particle receiving member suspended in the fluid in the sedimentation container for detecting the landing thereon of solid particles transferred from said dispenser; and
    means automatically responsive to the swinging movement of the particle dispenser for timing the landing of solid particles on the particle receiving member of said balance means and for determining the size of such particles.

9. Sedimentation-type particle size measuring apparatus for measuring the size of solid particles falling in a fluid of known viscosity, the apparatus comprising, in combination:
    a sedimentation container for the known-viscosity fluid;
    a particle dispenser for initially containing a sample of solid particles and disposed above the fluid in the sedimentation container, the particle dispenser having an open mouth portion and a lid carried by the dispenser and extending over only a part of the open mouth portion;
    ultrasonic means cooperating with the particle dispenser for dispersing solid particles therein;
    swingable support means supporting the particle dispenser for swinging movement and selectively actuable for swinging said particle dispenser so that the latter discharges said solid particles immediately above the fluid in the sedimentation container, and thereby rapidly transfers said solid particles from said dispenser to said sedimentation container, with the lid of the dispenser moving away from the open mouth portion thereof during the swinging of said dispenser;

balance means including a particle receiving member supported in the fluid in the sedimentation container for detecting the landing thereon of solid particles transferred from said dispenser; and means including an electrical circuit connected to the balance means for timing the landing of solid particles thereon and for determining the size of such particles.

10. Sedimentation-type particle size measuring apparatus for measuring the size of solid particles falling in a fluid of known viscosity, the apparatus comprising, in combination:

a sedimentation container for the known-viscosity fluid;

a cup-shaped particle dispenser for initially containing a sample of solid particles and disposed above the fluid in the sedimentation container, the particle dispenser having an open mouth portion and a lid pivotally carried by the dispenser and extending over only a part of the open mouth portion;

ultrasonic means cooperating with the particle dispenser for dispersing solid particles therein;

swingable support means supporting the particle dispenser for swinging movement and selectively actuable for swinging said particle dispenser so that the latter discharges said solid particles immediately above the fluid in the sedimentation container, and thereby rapidly transfers said solid particles from said dispenser to said sedimentation container, with the lid of the dispenser moving away from the open mouth portion thereof during the swinging of said dispenser;

balance means including a particle receiving member supported in the fluid in the sedimentation container for detecting the landing thereon of solid particles transferred from said dispenser; and means including an electrical circuit connected to the balance means for timing the landing of solid particles thereon and for determining the size of such particles.

11. Sedimentation-type solid particle size measuring apparatus for measuring the size of solid particles falling in a fluid of known viscosity, the apparatus comprising, in combination:

a sedimentation container for the known-viscosity fluid;

a cup-shaped particle dispenser for initially containing a sample of solid particles and disposed above the fluid in the sedimentation container, the particle dispenser having an open mouth portion and a lid pivotally carried by the dispenser and extending over only a part of the open mouth portion;

swingable support means supporting the particle dispenser for swinging movement and selectively actuable for swinging said particle dispenser so that the latter discharges said solid particles immediately above the fluid in the sedimentation container, and thereby rapidly transfers said solid particles from said dispenser to said sedimentation container, with the lid of the dispenser moving away from the open mouth portion thereof during the swinging of said dispenser;

ultrasonic means for dispersing said solid particles;

balance means including a particle receiving member supported in the fluid in the sedimentation container for detecting the landing thereon of solid particles transferred from said dispenser; and means including an electrical circuit connected to the balance means and automatically responsive to the swinging movement of the particle dispenser for timing the landing of solid particles on the particle receiving member and for determining the size of such particles.

12. Apparatus as defined in claim 11, in which the swingable support means includes a manually operable crank connected to the particle dispenser.

13. Apparatus as defined in claim 11, in which the ultrasonic means comprises a vibratory horn having a tip portion located a short distance beneath the surface of the particles within said dispenser.

14. Apparatus as defined in claim 11, in which the ultrasonic means comprises a vibratory ring-shaped member affixed to the inner periphery of the sedimentation container.

15. Sedimentation-type solid particle size measuring apparatus for measuring the size of solid particles falling in a fluid of known viscosity, the apparatus comprising, in combination:

a sedimentation container for the known-viscosity fluid;

a particle dispenser for initially containing a sample of solid particles and disposed above the fluid in the sedimentation container;

means selectively actuable for moving the particle dispenser above the surface of the fluid in the sedimentation container to rapidly transfer solid particles from said dispenser to said sedimentation container;

ultrasonic means carried by the sedimentation container and including a vibratory ring-shaped member for dispersing said solid particles;

balance means including a particle receiving member supported in the fluid in the sedimentation container for detecting the landing thereon of dispersed solid particles transferred from said dispenser; and means responsive to the detection of landing of solid particles onto the particle receiving member for determining the size of such particles.

16. Apparatus as defined in claim 15, in which the ring-shaped member is mounted beneath the surface of the fluid in the sedimentation container to disperse said solid particles following their transfer to said container.

17. Apparatus as defined in claim 15, in which the means responsive to the detection of the landing of said solid particles is operative to signal any weight differences of said particle receiving member at timed intervals beginning with the actuation of said selectively actuable means.

18. Sedimentation-type particle size measuring apparatus for measuring the size of solid particles falling in a fluid of known viscosity, the apparatus comprising, in combination:

a sedimentation container for the known-viscosity fluid;

a cup-shaped particle dispenser for initially containing a sample of solid particles and disposed above the fluid in the sedimentation container;

swingable support means supporting the particle dispenser for swinging movement and selectively actuable for swinging said particle dispenser so that the latter discharges said solid particles immediately above the surface of the fluid in the sedimentation container, and thereby rapidly transfers said solid particles from said dispenser to said sedimentation container;

balance means including a particle receiving member suspended in the fluid in the sedimentation container for detecting the of said landing thereon solid particles transferred from said dispenser; and means including an electrical circuit connected to the balance means for timing the landing of said solid particles thereby and for determining the size of the received particles.

19. Sedimentation-type particle size measuring apparatus for measuring the size of solid particles falling in a fluid of known viscosity, the apparatus comprising, in combination:

a sedimentation container for the known-viscosity fluid;

a cup-shaped particle dispenser for initially containing a sample of solid particles and disposed above the fluid in the sedimentation container, the particle dispenser having an open mouth portion and a lid pivotally carried by the dispenser and extending over only a part of the open mouth portion;

swingable support means supporting the particle dispenser for swinging movement and selectively actuable for swinging said particle dispenser so that the latter discharges said solid particles immediately above the surface of the fluid in the sedimentation container, and thereby rapidly transfers said solid particles from said dispenser to said sedimentation container;

balance means including a particle receiving member suspended in the fluid in the sedimentation container for detecting the landing thereon of said solid particles transferred from said dispenser; and means including an electrical circuit connected to the balance means for timing the landing of said solid particles thereon and for determining the size of such particles.

* * * * *